United States Patent
Colborn

(10) Patent No.: US 7,467,016 B2
(45) Date of Patent: Dec. 16, 2008

(54) MULTIPOLAR STIMULATION ELECTRODE WITH MATING STRUCTURES FOR GRIPPING TARGETED TISSUE

(75) Inventor: John Craig Colborn, League City, TX (US)

(73) Assignee: Cyberonics, Inc., Houston, TX (US)

( * ) Notice: Subject to any disclaimer, the term of this patent is extended or adjusted under 35 U.S.C. 154(b) by 559 days.

(21) Appl. No.: 11/341,306

(22) Filed: Jan. 27, 2006

(65) Prior Publication Data

US 2007/0179580 A1    Aug. 2, 2007

(51) Int. Cl.
*A61N 1/05* (2006.01)
(52) U.S. Cl. .................. 607/118; 607/149
(58) Field of Classification Search ............ 607/118
See application file for complete search history.

(56) References Cited

U.S. PATENT DOCUMENTS

| | | | |
|---|---|---|---|
| 3,421,511 A | 1/1969 | Terry, Jr. ............... 607/118 |
| 3,760,812 A | 9/1973 | Timm et al. ............ 607/116 |
| 3,774,618 A * | 11/1973 | Avery ................... 607/118 |
| 3,796,221 A | 3/1974 | Hagfors ................. 607/59 |
| 4,305,402 A | 12/1981 | Katims ................. 600/554 |
| 4,384,926 A | 5/1983 | Wagner ................. 205/122 |
| 4,459,989 A | 7/1984 | Borkan ................. 607/60 |
| 4,508,053 A | 4/1985 | Eriksson ............... 118/712 |
| 4,573,481 A | 3/1986 | Bullara ................. 607/118 |
| 4,590,946 A | 5/1986 | Loeb .................... 600/375 |
| 4,608,985 A | 9/1986 | Crish et al. ............ 607/74 |
| 4,612,934 A | 9/1986 | Borkan ................. 607/62 |
| 4,628,942 A | 12/1986 | Sweeney et al. ........ 607/118 |
| 4,649,936 A | 3/1987 | Ungar et al. ........... 607/118 |
| 4,702,254 A | 10/1987 | Zabara ................. 607/45 |
| 4,793,353 A | 12/1988 | Borkan ................. 607/60 |
| 4,850,356 A | 7/1989 | Heath .................. 607/42 |
| 4,860,616 A | 8/1989 | Smith .................. 76/4 |
| 4,867,164 A | 9/1989 | Zabara ................. 607/45 |
| 4,920,979 A | 5/1990 | Bullara ................ 607/118 |
| 4,979,511 A | 12/1990 | Terry, Jr. .............. 600/377 |
| 5,003,975 A | 4/1991 | Hafelfinger et al. ..... 607/28 |
| 5,025,807 A | 6/1991 | Zabara ................. 607/45 |
| 5,095,905 A | 3/1992 | Klepinski ............. 600/377 |
| 5,146,920 A | 9/1992 | Yuuchi et al. .......... 607/63 |
| 5,215,089 A | 6/1993 | Baker, Jr. ............. 600/377 |
| 5,251,634 A | 10/1993 | Weinberg .............. 600/377 |
| 5,344,438 A * | 9/1994 | Testerman et al. ....... 607/118 |
| 5,351,394 A | 10/1994 | Weinberg .............. 29/872 |
| 5,487,756 A * | 1/1996 | Kallesoe et al. ........ 607/118 |
| 5,531,778 A | 7/1996 | Maschino et al. ....... 607/118 |
| 5,575,813 A | 11/1996 | Edell et al. ........... 607/116 |
| 5,824,027 A * | 10/1998 | Hoffer et al. .......... 607/118 |

(Continued)

FOREIGN PATENT DOCUMENTS

EP    1145736    10/2001

*Primary Examiner*—Kennedy J Schaetzle
(74) *Attorney, Agent, or Firm*—Williams, Morgan & Amerson, P.C.; Timothy L. Scott

(57) ABSTRACT

An implantable electrode assembly for gripping nerves or other bodily structures is disclosed. The assembly comprises first and second spines containing first and second leads with at least one electrode cross rail joining the spines and at least one electrode providing a route for electrical conduction between the first and second lead. Mating structures on the spines allow the spines to be joined for securely attaching the assembly around the nerve.

20 Claims, 7 Drawing Sheets

U.S. PATENT DOCUMENTS

| | | | |
|---|---|---|---|
| 6,052,624 A | 4/2000 | Mann | 607/46 |
| 6,259,951 B1 | 7/2001 | Kuzma et al. | 607/57 |
| 6,304,787 B1 | 10/2001 | Kuzma et al. | 607/137 |
| 6,393,325 B1 | 5/2002 | Mann et al. | 607/46 |
| 6,418,348 B1 | 7/2002 | Witte | 607/122 |
| 6,473,653 B1 | 10/2002 | Schallhorn et al. | 607/116 |
| 6,477,417 B1 | 11/2002 | Levine | 607/9 |
| 6,510,332 B1 | 1/2003 | Greenstein | 600/377 |
| 6,600,956 B2 | 7/2003 | Maschino et al. | 607/118 |
| 6,606,523 B1 | 8/2003 | Jenkins | 607/133 |
| 6,609,025 B2 | 8/2003 | Barrett et al. | 607/2 |
| 6,907,295 B2 | 6/2005 | Gross et al. | 607/118 |
| 7,072,719 B2 * | 7/2006 | Vinup et al. | 607/117 |
| 2003/0078633 A1 * | 4/2003 | Firlik et al. | 607/46 |
| 2003/0144711 A1 | 7/2003 | Pless et al. | 607/60 |
| 2003/0236558 A1 | 12/2003 | Whitehurst et al. | 607/45 |
| 2004/0010303 A1 * | 1/2004 | Bolea et al. | 607/118 |
| 2004/0015205 A1 | 1/2004 | Whitehurst et al. | 607/48 |
| 2004/0167583 A1 | 8/2004 | Knudson et al. | 607/40 |
| 2004/0172088 A1 | 9/2004 | Knudson et al. | 607/40 |
| 2004/0172094 A1 | 9/2004 | Cohen et al. | 607/48 |
| 2005/0010265 A1 * | 1/2005 | Baru Fassio et al. | 607/48 |
| 2005/0016657 A1 | 1/2005 | Bluger | 156/50 |
| 2005/0038484 A1 | 2/2005 | Knudson et al. | 607/40 |
| 2005/0131485 A1 | 6/2005 | Knudson et al. | 607/40 |
| 2005/0203599 A1 * | 9/2005 | Garabedian et al. | 607/116 |
| 2006/0030919 A1 * | 2/2006 | Mrva et al. | 607/118 |
| 2006/0058597 A1 | 3/2006 | Machado et al. | 600/373 |
| 2006/0271137 A1 * | 11/2006 | Stanton-Hicks | 607/118 |
| 2007/0027514 A1 * | 2/2007 | Gerber | 607/116 |
| 2007/0173914 A1 * | 7/2007 | Kollatschny | 607/116 |
| 2008/0172116 A1 * | 7/2008 | Mrva et al. | 607/115 |

* cited by examiner

MULTIPOLAR STIMULATION ELECTRODE WITH MATING STRUCTURES FOR GRIPPING TARGETED TISSUE

BACKGROUND OF THE INVENTION

1. Field of the Invention

The present invention relates generally to apparatus for electrical stimulation of structures within the body. More particularly, it concerns apparatus for electrical stimulation of cylindrical bodies, such as cranial nerves, within the human body.

2. Description of Related Art

The human nervous system (HNS) includes the brain and the spinal cord, collectively known as the central nervous system (CNS). The central nervous system comprises nerve fibers that transmit nerves to, from, and within the brain and spinal cord. The network of nerves in the remaining portions of the human body forms the peripheral nervous system (PNS). Some peripheral nerves connect directly to the brain to control various brain functions, such as vision, eye movement, hearing, facial movement, and feeling. Another system of peripheral nerves, known as the autonomic nervous system (ANS), controls blood vessel diameter, intestinal movements, and actions of many internal organs. Autonomic functions include blood pressure, body temperature, heartbeat and essentially all the unconscious activities that occur without voluntary control.

Like the rest of the human nervous system, nerve signals travel up and down the peripheral nerves, which link the brain to the rest of the human body. Many, but not all, nerve fibers in the brain and the peripheral nerves are sheathed in a covering called myelin. The myelin sheath insulates electrical pulses traveling along the nerves. A nerve bundle may comprise up to 100,000 or more individual nerve fibers of different types, including larger diameter A and B fibers which comprise a myelin sheath and C fibers which have a much smaller diameter and are unmyelinated. Different types of nerve fibers, among other things, comprise different sizes, conduction velocities, stimulation thresholds, and myelination status (i.e., myelinated or unmyelinated).

Cranial nerve stimulation, such as electrical stimulation of the vagus nerve, has been used to treat a number of nervous system disorders, including epilepsy and other movement disorders, depression and other neuropsychiatric disorders, dementia, coma, migraine headache, obesity, eating disorders, sleep disorders, cardiac disorders (such as congestive heart failure and atrial fibrillation), hypertension, non-reproductive endocrine disorders (such as diabetes and hypoglycemia), and pain, among others. See, e.g., U.S. Pat. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. One known electrode design for cranial nerve stimulation involves an electrode assembly containing a plurality of helical electrodes wrapped about a cranial nerve, wherein the electrode assembly is secured to the nerve by a spiral anchoring tether, such as that disclosed in U.S. Pat. No. 4,979,511 issued Dec. 25, 1990 to Reese S. Terry, Jr. and assigned to the same assignee as the instant application.

Though effective, electrode assemblies known in the art may, in certain applications, have room for improvement in their abilities to grip a nerve or other bodily structure. Also, they may have room for improvement in their abilities to maximize current flow through a targeted bodily structure, such as a nerve, and minimize current flow outside of the targeted bodily structure, such as to a tissue structure nearby in a patient's body. Such flow of leakage current around the tissue structure proximate the implanted electrode may adversely affect normal functioning of non-targeted tissue regions.

SUMMARY OF THE INVENTION

In one embodiment, the present invention relates to an electrode assembly including a first spine having a first end, a second end, and at least one first mating structure; a second spine having a first end, a second end, and at least one second mating structure, wherein the first spine is generally opposite to the second spine, and wherein the first mating structure is capable of mating with the second mating structure; a first lead housed at least partially within the first spine, wherein the first lead extends from the first end of the first spine through at least a portion of the first spine; a second lead housed at least partially within the second spine, wherein the second lead extends from the first end of the second spine through at least a portion of the second spine; at least one electrode providing a route for electrical conduction between the first lead to the second lead; a first rail joining the first spine and the second spine at a position near the first ends of the first and second spines and angled toward the first ends; and a second rail joining the first spine and the second spine at a position near the second ends of the first and second spines and angled toward the second ends.

In another embodiment, the present invention relates to an electrode assembly including a first spine having a first end and a second end; a second spine having a first end and a second end, wherein the first spine is generally opposite to the second spine, wherein the first spine and the second spine are joinable at the first end of the first spine and the first end of the second spine, and wherein the first spine and the second spine are formed of an electrically nonconductive material; a first lead housed at least partially within the first spine, wherein the first lead extends from the first end of the first spine through at least a portion of the first spine; a second lead housed at least partially within the second spine, wherein the second lead extends from the first end of the second spine through at least a portion of the second spine; at least one electrode cross rail joining the first spine and the second spine, wherein the at least one electrode cross rail is formed of an electrically nonconductive material; at least one electrode housed at least partially within the electrode cross rail and providing a route for electrical conduction between the first lead to the second lead; a first rail joining the first spine and the second spine at a position closer to the first ends of the first and second spines relative to the at least one electrode cross rail, wherein the first rail is substantially formed of an electrically nonconductive material; a second rail joining the first spine and the second spine at a position closer to the second ends of the first and second spines relative to the at least one electrode cross rail, wherein the second rail is substantially formed of an electrically nonconductive material; and at least one electrically nonconductive membrane, wherein each membrane glazes a window defined by the first spine, the second spine, and two other rails selected from the group consisting of the electrode cross rail or rails, the first rail, and the second rail.

In another embodiment, the present invention relates to an implantable medical system including an implantable medical device including a controller to provide an electrical signal for performing neuromodulation; and an electrode assembly including a first spine having a first end and a second end; a second spine having a first end and a second end, wherein the first spine is generally opposite to the second spine, wherein the first spine and the second spine are joinable at the first end of the first spine and the first end of the second spine, and wherein the first spine and the second spine are formed of an electrically nonconductive material; a first lead housed at least partially within the first spine, wherein the first lead extends from the first end of the first spine through at least a portion of the first spine; a second lead housed at least partially within the second spine, wherein the second lead extends from the first end of the second spine through at least a portion of the second spine; at least one electrode cross rail joining the first spine and the second spine, wherein the at least one electrode cross rail is formed of an electrically nonconductive material; at least one electrode housed at least partially within the electrode cross rail and providing a route for electrical conduction between the first lead to the second lead; a first rail joining the first spine and the second spine at a position closer to the first ends of the first and second spines relative to the at least one electrode cross rail, wherein the first rail is substantially formed of an electrically nonconductive material; a second rail joining the first spine and the second spine at a position closer to the second ends of the first and second spines relative to the at least one electrode cross rail, wherein the second rail is substantially formed of an electrically nonconductive material.

In yet another embodiment, the present invention relates to an electrode assembly including a first spine having at least one first mating structure, a second spine having at least one second mating structure, wherein the first spine is generally opposite to the second spine, wherein the first mating structure is capable of mating with the second mating structure, and wherein the first spine and the second spine are formed substantially from an electrically nonconductive material capable of insulating a first body tissue from electrical current; and an electrode housed at least partially within at least one of the first spine and the second spine, wherein the electrode is capable of providing electrical current to stimulate a second body tissue.

The electrode assembly of the present invention may have an improved ability to grip a nerve or other bodily structure relative to known electrode assemblies. Also, it may have an improved ability to maximize current flow through a targeted bodily structure and minimize current flow outside of the targeted bodily structure.

BRIEF DESCRIPTION OF THE DRAWINGS

The invention may be understood by reference to the following description taken in conjunction with the accompanying drawings, in which like reference numerals identify like elements, and in which.

Figure 1:
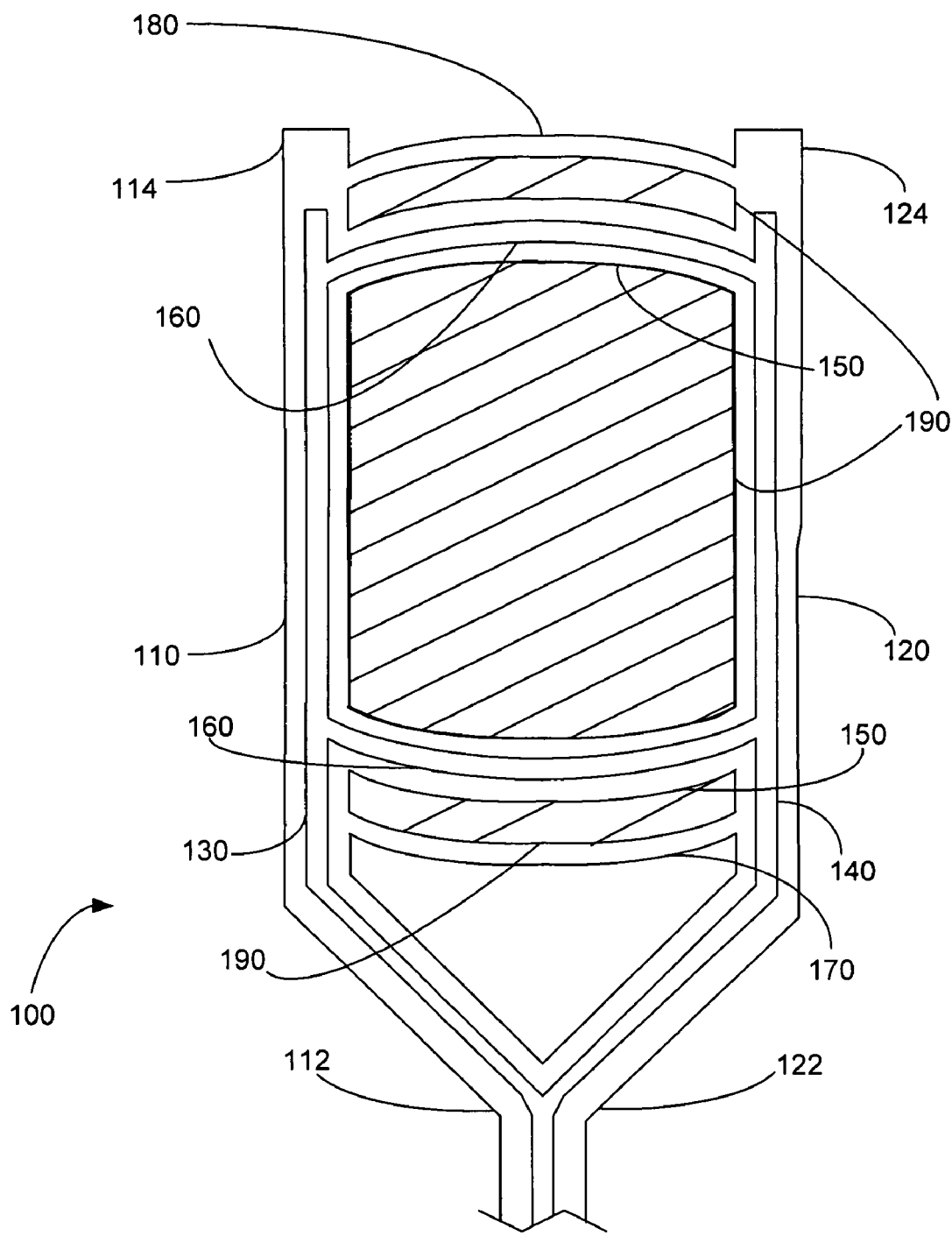
FIG. 1 illustrates an electrode assembly according to one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DESCRIPTION OF ILLUSTRATIVE EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

Certain terms are used throughout the following description and claims refer to particular system components. As one skilled in the art will appreciate, components may be referred to by different names. This document does not intend to distinguish between components that differ in name but not function. In the following discussion and in the claims, the terms "include" and "including" are used in an open-ended fashion, and thus should be interpreted to mean "including, but not limited to." Also, the term "couple" or "couples" is intended to mean either a direct or an indirect electrical connection. For example, if a first device couples to a second device, that connection may be through a direct electrical connection or through an indirect electrical connection via other devices, biological tissues, or magnetic fields. "Direct contact," "direct attachment," or providing a "direct coupling" indicates that a surface of a first element contacts the surface of a second element with no substantial attenuating medium therebetween. The presence of substances, such as bodily fluids, that do not substantially attenuate electrical connections does not vitiate direct contact. The word "or" is used in the inclusive sense (i.e., "and/or") unless a specific use to the contrary is explicitly stated.

In one embodiment of the present invention, methods, apparatus, and systems comprising a multipolar electrode are provided to apply an electrical signal to an autonomic nerve such as a cranial nerve (e.g., a vagus nerve) to treat one or more disorders (e.g., a mood disorder, an epilepsy disorder, an eating disorder, a hormonal disorder, a reproductive disorder, a metabolic disorder, a hearing disorder, a pain disorder, and/or a heart rhythm disorder, among others). Application of an electrical signal to the nerve refers to delivery of electrical signal (i.e., a pulsed or non-pulsed electrical current) to the nerve from a source external to the nerve, e.g., an implanted neurostimulator. In general, the term "electrical signal" thus refers to an exogenous electrical signal generated by the medical device and applied to a nerve, in contrast to endogenous or native electrical activity comprising afferent and efferent action potentials, hyperpolarizations, and subthreshold depolarizations that are generated by the patient's body. The electrode assembly disclosed herein may be operably coupled to a neurostimulator and used in methods of electrical stimulation of any cranial nerve, such as the vagus nerve (cranial nerve X). A generally suitable form of neurostimulator for use with the apparatus of the present invention is disclosed, for example, in U.S. Pat. No. 5,154,172, assigned to the same assignee as the present application. A commercially available neurostimulator system referred to as a VNS Therapy™ Pulse Generator is available from Cyberonics, Inc., Houston, Tex., the assignee of the present application. Certain parameters of the electrical signal generated by the neurostimulator are programmable, such as by means of an external programmer in a manner conventional for implantable electrical medical devices.

Embodiments of the present invention provide for a multipolar electrode which may be used with a neurostimulator system for treatment of disorders, e.g., a mood disorder, an epilepsy disorder, an eating disorder, a hormonal disorder, a reproductive disorder, a metabolic disorder, a hearing disorder, a pain disorder, and/or a heart rhythm disorder, among others.

In one embodiment, the present invention relates to an electrode assembly including a first spine having at least one first mating structure and a second spine having at least one second mating structure, wherein the first spine is generally opposite to the second spine. In a particular embodiment, the first spine is substantially parallel to the second spine. The first mating structure is capable of mating with the second mating structure.

Figure 2:
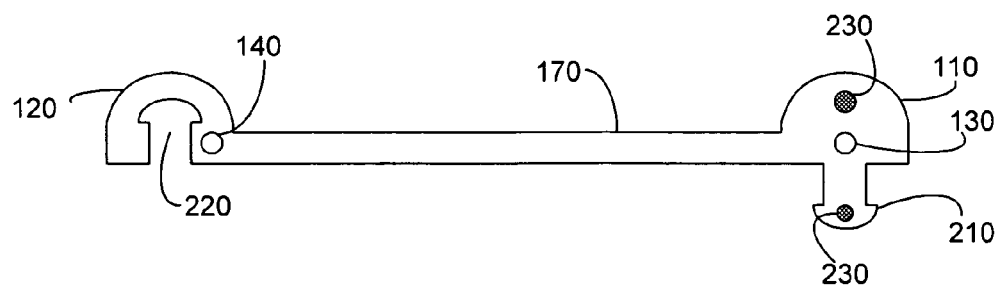
FIG. 2 illustrates in cross-section one embodiment of snap-fit mating structures of an electrode assembly in accordance with an illustrative embodiment of the present invention.

One particular embodiment of an electrode assembly is shown in FIG. 1 (top-down) and FIG. 2 (cross-section). The electrode assembly 100 includes a first spine 110 having a first end 112 and a second end 114. In one embodiment, the first spine 110 may also include at least one first mating structure 210. The electrode assembly 100 also includes a second spine 120 having a first end 122 and a second end 124. In one embodiment, the second spine 120 may also include at least one second mating structure 220. In the electrode assembly 100, the first spine 110 is generally opposite to the second spine 120. As shown in FIG. 1, the first spine 110 may be substantially parallel to the second spine 120 for at least a portion of the length of the first and second spines 110, 120. The first spine 110 and the second spine 120 are joinable at the first end 112 of the first spine 110 and the first end 122 of the second spine 120. Both the first spine 110 and the second spine 120 may be formed of an electrically nonconductive material, such as silicone, among others. In embodiments wherein the first spine 110 and the second spine 120 contain mating structures 210, 220, the first mating structure 210 may be capable of mating with the second mating structure 220.

Housed at least partially within the first spine 110 is a first lead 130. The first lead 130 extends from the first end 112 of the first spine 110 through at least a portion of the first spine 110. Housed at least partially within the second spine 120 is a second lead 140. The second lead 140 extends from the first end 122 of the second spine 120 through at least a portion of the second spine 120. The first lead 130 and the second lead 140 may be formed of any electrically conductive material or materials. The first lead 130 and the second lead 140 may join at the first ends 112, 122 and may be in electrical current communication with a lead (FIG. 3, element 320) and subsequently to an electrical signal generator, such as a neurostimulator (not shown).

The electrode assembly 100 also contains at least one electrode cross rail 150 joining the first spine 110 and the second spine 120. The electrode assembly 100 may contain one, two, three, or more electrode cross rails 150. The at least one electrode cross rail 150 may be formed of an electrically nonconductive material, such as silicone, among others. In general, the spines, rails, and membranes described herein may be formed of one or more electrically nonconductive materials. Any electrically nonconductive material, containing one or more chemical compounds that assist in imparting electrical nonconductivity to the material, may be used. In one embodiment, the electrical nonconductive material(s) may be selected from the group consisting of silicones and urethanes. The invention is not limited to these materials. The electrically nonconductive material(s) substantially cover(s) (shields from direct physical contact with bodily tissues, fluids, or other materials) the leads and electrodes described above, and in one embodiment completely cover(s) the leads and electrodes. In one embodiment, the material is flexible and biocompatible.

Housed within the at least one electrode cross rail 150 is an electrode 160. The electrode 160 provides a route for electrical conduction between the first lead 130 and the second lead 140. The electrode 160 may be formed of any electrically conductive material.

The first lead 130, the second lead 140, and the electrode(s) 160 may contain any number of circuit elements such that electrical fields of substantially any desired magnitude, polarity, and direction may be induced in materials in proximity to the electrode assembly 100 upon the flow of electric current through and among the first lead 130, the second lead 140, and the electrode(s) 160.

The electrode assembly 100 also contains a first rail 170 joining the first spine 110 and the second spine 120 at a position closer to the first ends 112, 122 of the first and second spines 110, 120 relative to the at least one electrode cross rail 150. The first rail 170 may be substantially formed of an electrically nonconductive material and may also be relatively flexible. The first rail 170 may provide insulation against current flow in either direction between the at least one electrode 160 and the first ends 112, 122. The first rail 170 may provide mechanical support for the electrode assembly 100, as shown in embodiments described below.

The electrode assembly 100 also contains a second rail 180 joining the first spine 110 and the second spine 120 at a position closer to the second ends 114, 124 of the first and second spines 110, 120 relative to the at least one electrode cross rail 150. The second rail 180 may be substantially formed of an electrically nonconductive material and may also be relatively flexible. The second rail 180 may provide insulation against current flow in either direction between the at least one electrode 160 and the first ends 112, 122. The second rail 180 may provide mechanical support for the electrode assembly 100, as shown in embodiments described below.

The electrode assembly 100 also includes at least one electrically nonconductive membrane 190. FIG. 1 shows three membranes 190. The membrane 190 may be formed from silicone or another elastomeric electrically nonconductive material. The membrane 190 may be formed from a material that permits osmotic flow, liquid flow, or solute diffusion thereacross.

In one embodiment, the electrically nonconductive membrane 190 is thinner than the first spine 110, the second spine 120, the electrode cross rail 150, the first rail 170, and the second rail 180. "Thinner" is defined as having a thickness in the cross section shown in FIG. 2 which is less than the thickness of the other listed elements of the electrode assembly 100.

As is apparent from FIG. 1, various elements of the electrode assembly 100 can be considered to define one or more windows defined by the first spine 110, the second spine 120, and two other rails selected from the group consisting of the electrode cross rail or rails 150, the first rail 170, and the second rail 180. Each membrane 190 glazes at least one window. In one embodiment, each window as defined according to this paragraph is glazed by a membrane 190.

As stated above, in one embodiment the first spine 110 contains a first mating structure 210 and the second spine 120 contains a second mating structure 220. FIG. 2 illustrates in cross-section one embodiment of the first mating structure 210 and the second mating structure 220, wherein the first mating structure 210 is a male snap-fit structure and the second mating structure 220 is a female snap-fit structure. Other types of mating structures will be apparent to the skilled artisan having the benefit of the present disclosure. The mating structures 210, 220 may be discrete structures spaced at intervals along the length of the first spine 110 and the second spine 120, or they may be continuous structures running in a strip along the length of the first spine 110 and the second spine 120. Mating of the first mating structure 210 and the second mating structure 220 according to this embodiment will be described below.

In another embodiment, the electrode assembly 100 of FIG. 2 can further include a mating element having a male end and a female end, wherein the male end is capable of snap-fitting with the second mating structure 220 and the female end is capable of snap-fitting with the first mating structure 210. The mating element of this embodiment can allow an implanting surgeon greater control over the size, rigidity, or both of the electrode assembly 100.

In another embodiment, in the electrode assembly 100, the first mating structure may be a female structure and the second mating structure may also be a female structure. In this embodiment, the electrode assembly 100 may further contain a mating element having a first male end and a second male end, wherein the first male end is capable of snap-fitting with the second mating structure and the second male end is capable of snap-fitting with the first mating structure. The mating element of this embodiment can allow an implanting surgeon greater control over the size, rigidity, or both of the electrode assembly 100.

If desired, the electrode assembly 100 may further contain stiffening material 230. The stiffening material 230 may be housed at least partially within and extend through at least a portion of the first spine 110, the second spine 120, the first rail 170, the second rail 180, or two or more thereof. In one embodiment, the stiffening material 230 may be housed at least partially within and extend through at least a portion of the first spine 110. Stiffening material 230 may also be housed at least partially within and extend through at least a portion of a mating structure, such as first mating structure 210.

Figure 3:
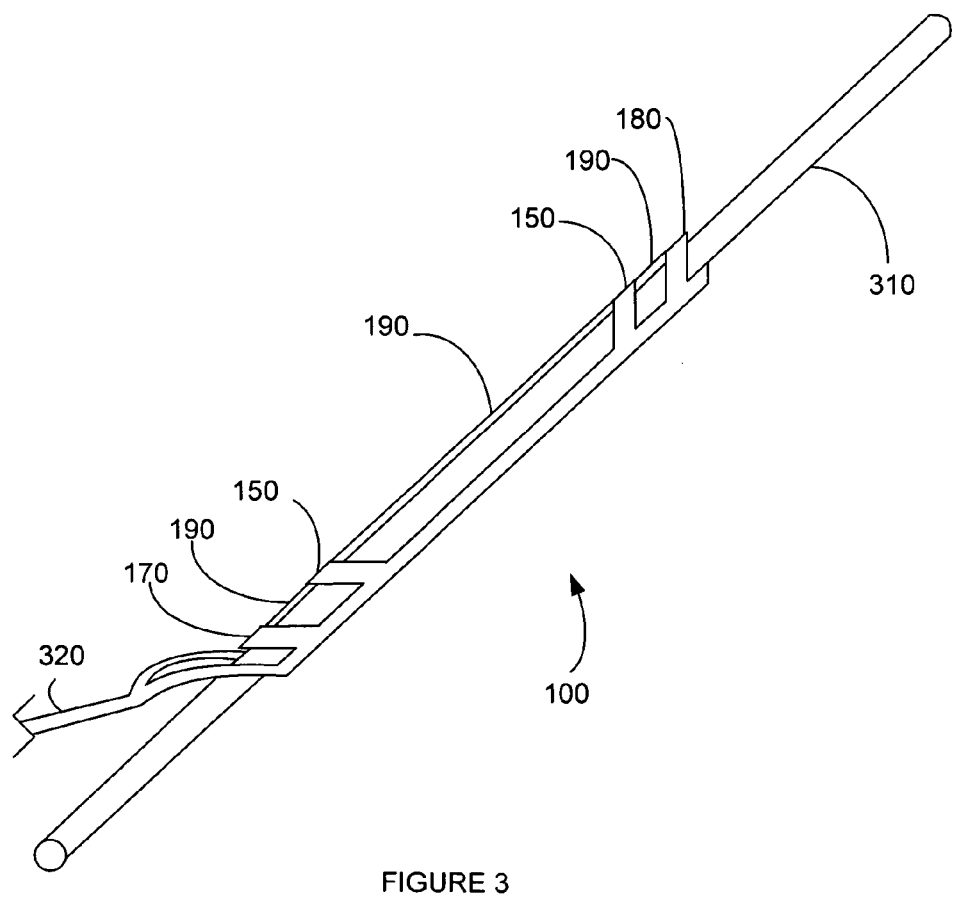
FIG. 3 illustrates an electrode assembly attached to a nerve according to one illustrative embodiment of the present invention.
Figure 4:
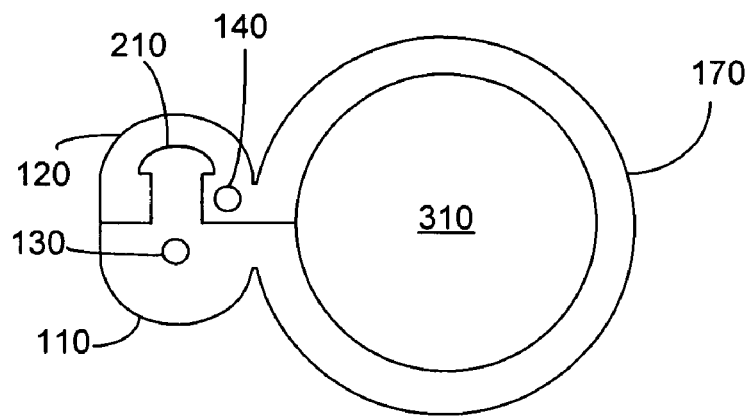
FIG. 4 illustrates in cross-section one embodiment of snap-fit mating structures of an electrode assembly attached to a nerve, in accordance with one illustrative embodiment of the present invention.

Turning to FIG. 3 and FIG. 4, in one embodiment, the electrode assembly 100 may be attached to a nerve 310, such as a cranial nerve, such as the vagus nerve, by mating the first mating structure 210 and the second mating structure 220. The attachment may be performed by laying the electrode assembly 100 in its unmated state (FIG. 2) on the nerve 310 with the first spine 110 and second spine 120 generally parallel to the axis of the nerve 310 and then mating the first mating structure 210 and the second mating structure 220 by curving the electrode assembly 100 transversely around the nerve 310 (FIG. 4). This allows the electrode assembly 100 to be securely attached to the nerve 310 while imparting a relatively low amount of mechanical stress to the nerve 310.

Figure 5A:
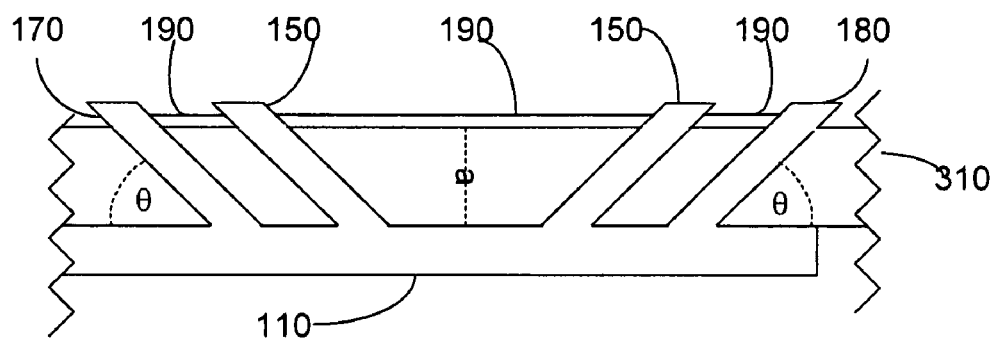
FIGS. 5A-5B illustrate in side view one embodiment of angled rails of an electrode assembly attached to a nerve, in accordance with one illustrative embodiment of the present invention.
Figure 5B:
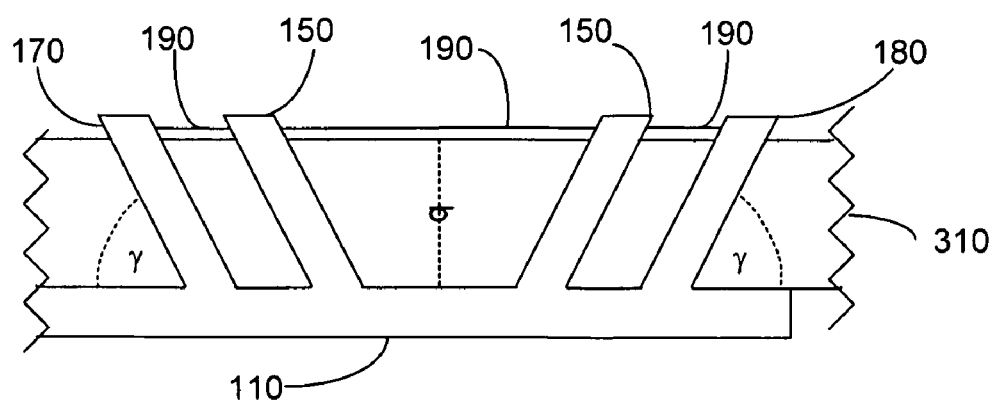

In one embodiment, in the electrode assembly 100, one or both of the first rail 170 and the second rail 180 are angled toward the nearest of the first end 112, 122 or the second end 114, 124 of the first spine 110 and the second spine 120. As shown in FIGS. 5A-5B, angling of one or both of the first rail 170 and the second rail 180, in combination with relative flexibility of one or both of the first rail 170 and the second rail 180, may allow the electrode assembly 100 to be readily attached to nerves 310 of different dimensions (a and b) by enabling the first and second rails 170, 180 to distend to angles θ and γ as needed to facilitate nerve/electrode contact.

In one embodiment, the first rail 170 and the second rail 180 carry a mechanical load and the at least one electrode cross rail 150 does not carry a mechanical load.

In another embodiment, the electrode assembly 100 may be attached in a planar fashion to a part of the body, such as the outer stomach wall. In a planar attachment, one or more of the first spine 110, the second spine 120, the first rail 170, and the second rail 180 may be used by a surgeon as an anchor point for suturing. An electrode assembly 100 for planar attachment need not have, but may possess, mating structures 210, 220.

In one embodiment, the thickness of the electrode assembly 100 (the vertical dimension in FIG. 2, excluding the thickness of the mating structures 210, 220) is substantially smaller than the width of the electrode assembly 100 (the distance between the outermost points of the first spine 110 and the second spine 120).

As stated above, the first lead 130, the second lead 140, and the at least one electrode 160 may be constructed to form a circuit generating one or more electrical fields of desired magnitude, polarity, and direction. This can be useful for imparting electrical stimulation to a body structure, such as a body structure having a long axis, such as a nerve. Such construction is a routine matter for the skilled artisan having the benefit of the present disclosure.

Figure 6A:
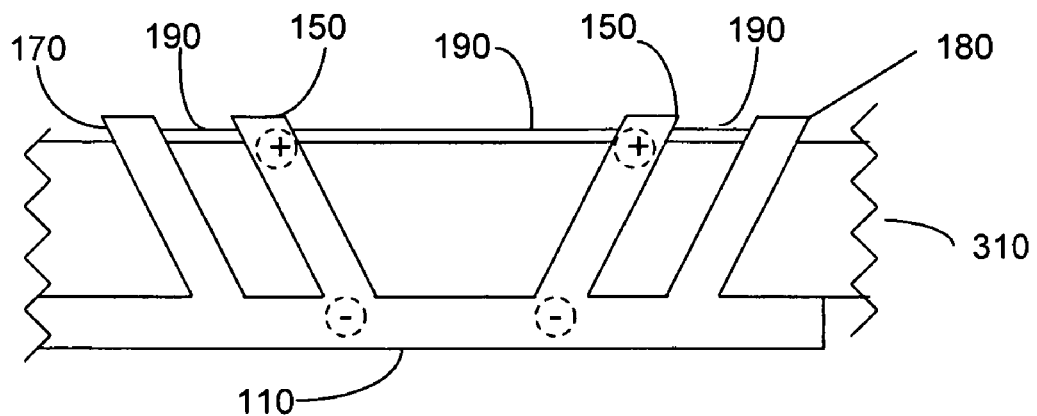
FIGS. 6A-6B illustrate in side view two embodiments of imposing electrical potential across or along a nerve through the use of an electrode assembly attached to a nerve, in accordance with illustrative embodiments of the present invention.
Figure 6B:
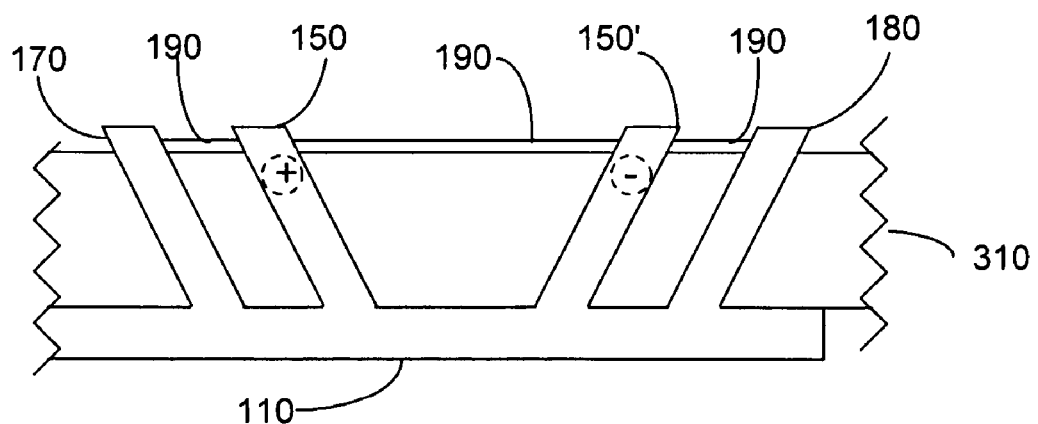

FIGS. 6A-6B illustrate in side view several embodiments of current direction possible by use of an electrode assembly 100 according to the present invention and having two electrodes 160, each in an electrode cross rail 150. The electrode assembly 100 is attached to a body structure (in the illustrated embodiment, a nerve 310 having a long axis substantially parallel to the first rail 110 and the second rail 120). In the interest of clarity, the first and second leads 130, 140 and the at least one electrode 160 are not shown in FIGS. 6A-6B. The second spine 120 is behind the first spine 110 and is not shown in FIGS. 6A-6B. In FIG. 6A, the electrode assembly 100 may be configured to provide current flow perpendicular to the long axis of the body structure, specifically in the illustrated embodiment, transversely across the nerve 310, providing a neuromodulation effect. As will be apparent to the skilled artisan having the benefit of the present disclosure, the same effect but with the opposite current flow direction can be produced by modifying the configuration of the electrode assembly 100 or reversing the direction of current flow therethrough.

In FIG. 6B, the electrode assembly 100 may be configured to provide current flow parallel to the long axis of the body structure, specifically in the illustrated embodiment, longitudinally along the nerve 310, between one electrode cross rail 150 and another electrode cross rail 150'. As will be apparent to the skilled artisan having the benefit of the present disclosure, the same effect but with the opposite current flow direction can be produced by modifying the configuration of the electrode assembly 100 or reversing the direction of current flow therethrough. Other combinations of current flow direction are possible and within the scope of the present invention.

More generally, the endogenous electrical activity (i.e., activity attributable to the natural functioning of the patient's own body) of a neural structure of a patient may be modulated in a variety of ways. In particular, the electrical activity may be modulated by exogenously applied (i.e., from a source other than the patient's own body) electrical, chemical, or mechanical signals applied to the neural structure. The modulation (which may be referred to generally as "neurostimulation" or "neuromodulation") may involve the induction by the generation of afferent action potentials, efferent action potentials, or both, in the neural structure, and may also involve blocking or interrupting the transmission of endogenous electrical activity traveling along the nerve. Electrical neurostimulation or modulation of a neural structure refers to the application of an exogenous electrical signal (as opposed to a chemical or mechanical signal), to the neural structure. Electrical neurostimulation may be provided by implanting an electrical device underneath the skin of a patient and delivering an electrical signal to a nerve such as a cranial nerve. The electrical neurostimulation may involve performing a detection, with the electrical signal being delivered in response to a detected body parameter. This type of stimulation is generally referred to as "active," "feedback," or "triggered" stimulation. Alternatively, the system may operate without a detection system once the patient has been diagnosed with epilepsy (or another medical condition), and may periodically apply a series of electrical pulses to the nerve (e.g., a cranial nerve such as a vagus nerve) intermittently throughout the day, or over another predetermined time interval. This type of stimulation is generally referred to as "passive," "non-feedback," or "prophylactic," stimulation. The stimulation may be applied by an implantable medical device that is implanted within the patient's body.

Figure 7A:
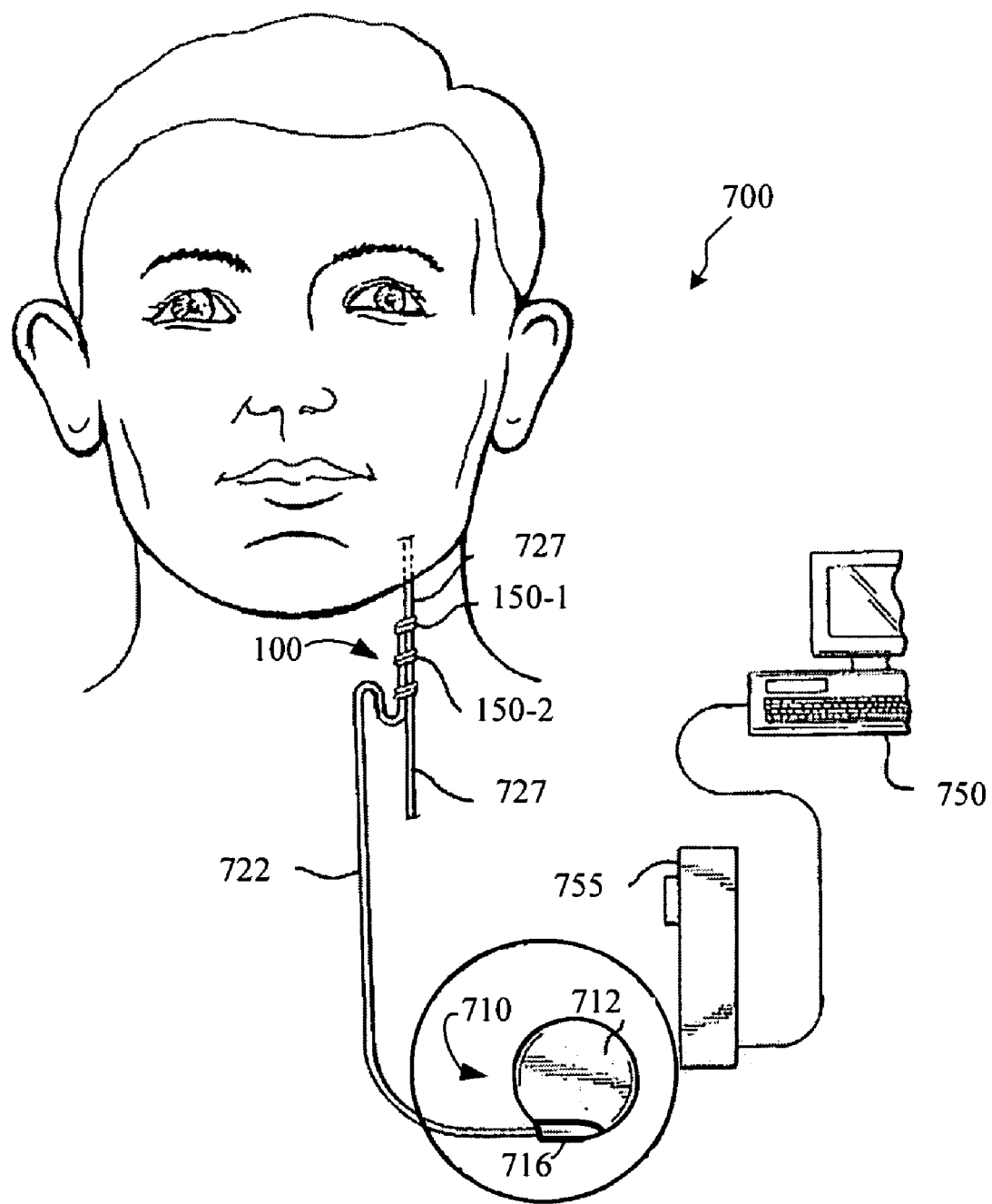
FIGS. 7A-7C provide stylized diagrams of an implantable medical device implanted into a patient's body for providing an electrical signal to a portion of the patient's body, in accordance with one illustrative embodiment of the present invention.
Figure 7B:
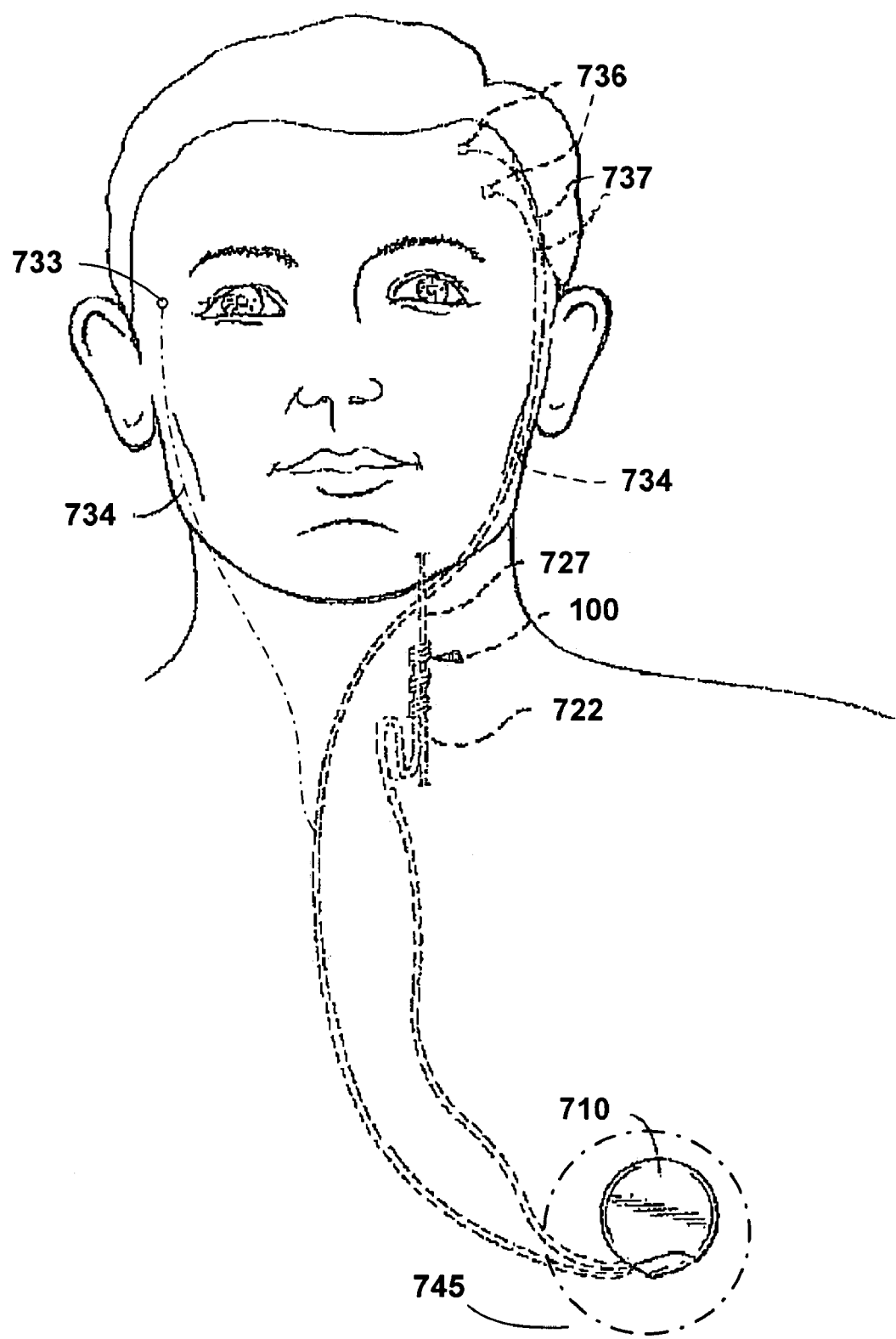
Figure 7C:
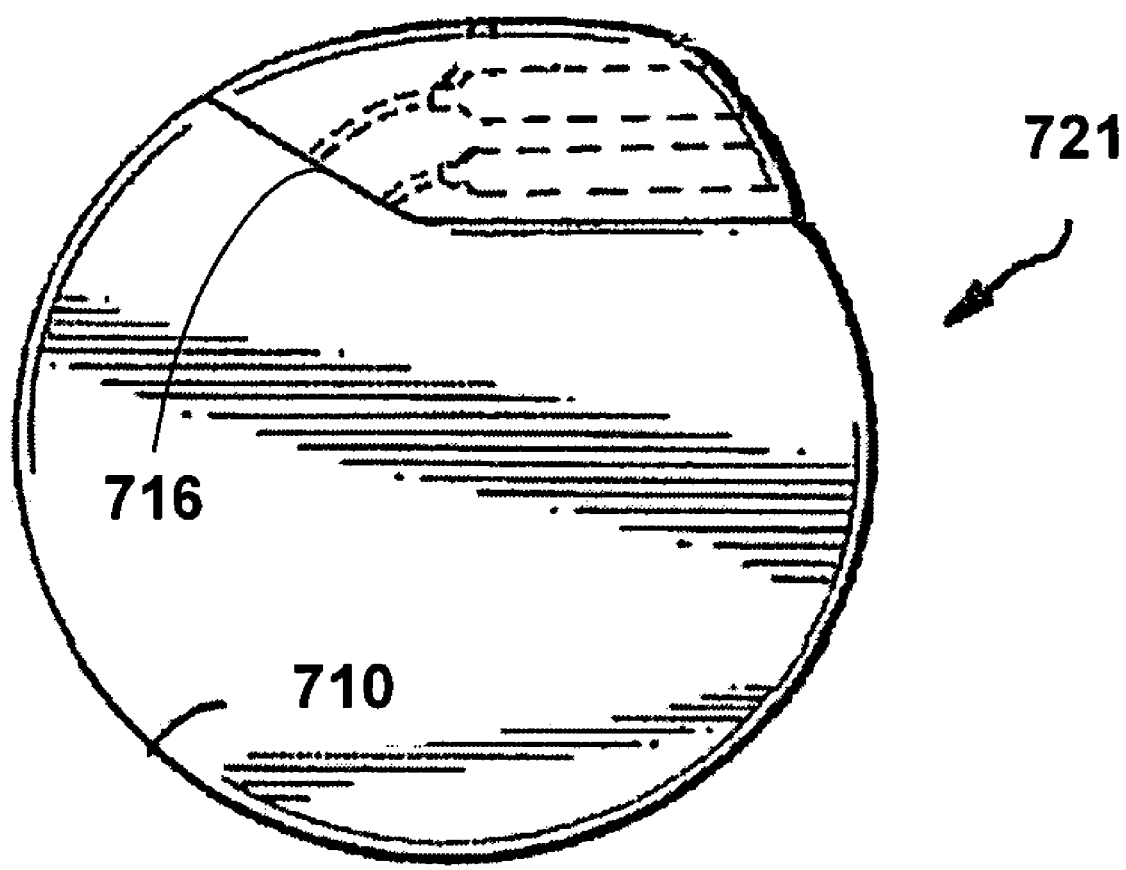

Although not so limited, a system capable of implementing embodiments of the present invention is described below. FIGS. 7A-7C depict a stylized implantable medical system 700 for implementing one or more embodiments of the present invention. FIGS. 7A-7C illustrate an electrical signal generator 710 having main body 712 comprising a case or shell 721 (FIG. 7C) with a header 716 (FIG. 7A) for connecting to leads 722. The generator 710 may be implanted in the patient's chest in a pocket or cavity formed by the implanting surgeon just below the skin (indicated by a dotted line 745, FIG. 7B), similar to the implantation procedure for a pacemaker pulse generator.

A stimulating nerve electrode assembly 100 is conductively connected to the distal end of an insulated, electrically conductive lead assembly 722, which may comprise one lead wire or a plurality of lead wires. The stimulating nerve electrode assembly 100 may comprise a plurality of electrodes 150, such as two electrodes 150-1, 150-2. Lead assembly 722 is attached at its proximal end to a connector or connectors on the header 716 on case 721. The electrode assembly 100 may be surgically coupled to a vagus nerve 727 in the patient's neck or at another location, e.g., near the patient's diaphragm. Other cranial nerves may also be used to deliver the electrical neurostimulation signal. In one embodiment, the electrode assembly 100 preferably comprises a multipolar electrode, as described herein. However, persons of skill in the art will appreciate that many electrode designs could be used in the present invention. The electrode assembly 100 may be used with systems further containing sensory electrodes, for example, sensory electrode 733 served by lead 734 in FIG. 7B, or other stimulation electrodes, such as electrodes 736 served by leads 737 in FIG. 7B.

All of the apparatus disclosed and claimed herein may be made and executed without undue experimentation in light of the present disclosure. While the apparatus of this invention have been described in terms of particular embodiments, it will be apparent to those of skill in the art that variations may be applied to the apparatus described herein without departing from the concept, spirit and scope of the invention as defined by the appended claims. It should be especially apparent that the principles of the invention may be applied to selected body structures other than the vagus nerve, for example, other cranial nerves, other neural structures, and other body structures, including organ structures, among others, to achieve particular results.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. An electrode assembly, comprising:
   a first spine having a first end and a second end and at least one first mating structure;
   a second spine having a first end and a second end and at least one second mating structure, wherein said first spine is generally opposite to said second spine, and wherein said first mating structure is capable of mating with said second mating structure;
   a first lead housed at least partially within said first spine, wherein said first lead extends from the first end of the first spine through at least a portion of the first spine;
   a second lead housed at least partially within said second spine, wherein said second lead extends from the first end of the second spine through at least a portion of the second spine;
   at least one electrode providing a route for electrical conduction between said first lead and said second lead;
   a first rail joining said first spine and said second spine at a position near the first ends of the first and second spines and angled toward one of said first ends and said second ends of said first and second spines; and
   a second rail joining said first spine and said second spine at a position near the second ends of said first and second spines and angled toward one of said first ends and said second ends of said first and second spines.

2. An electrode assembly, comprising:
   a first spine having a first end and a second end;
   a second spine having a first end and a second end, wherein said first spine is generally opposite to said second spine, wherein the first spine and the second spine are joinable at the first end of said first spine and the first end of said second spine, and wherein said first spine and said second spine are formed of an electrically nonconductive material;
   a first lead housed at least partially within said first spine, wherein said first lead extends from the first end of the first spine through at least a portion of the first spine;

a second lead housed at least partially within said second spine, wherein said second lead extends from the first end of the second spine through at least a portion of the second spine;

at least one electrode cross rail joining said first spine and said second spine, wherein said at least one electrode cross rail is formed of an electrically nonconductive material;

at least one electrode housed at least partially within the electrode cross rail and providing a route for electrical conduction between said first lead and said second lead;

a first rail joining said first spine and said second spine at a position closer to the first ends of the first and second spines relative to said at least one electrode cross rail, wherein said first rail is substantially formed of an electrically nonconductive material;

a second rail joining said first spine and said second spine at a position closer to the second ends of said first and second spines relative to said at least one electrode cross rail, wherein said second rail is substantially formed of an electrically nonconductive material; and at least one electrically nonconductive membrane, wherein said at least one membrane glazes a window defined by said first spine, said second spine, and two other rails selected from the group consisting of said at least one electrode cross rail, said first rail, and said second rail.

3. The electrode assembly of claim 2, wherein at least one of said first spine, said second spine, said first rail, said second rail, and said at least one electrode cross rail, comprises silicone.

4. The electrode assembly of claim 2, wherein said at least one electrically nonconductive membrane comprises silicone.

5. The electrode assembly of claim 2, wherein the first spine further comprises at least one first mating structure, the second spine further comprises at least one second mating structure, and wherein said first mating structure is capable of mating with said second mating structure.

6. The electrode assembly of claim 5, wherein said first mating structure is a male snap-fit structure and said second mating structure is a female snap-fit structure.

7. The electrode assembly of claim 6, further comprising a mating element having a male end and a female end, wherein the male end is capable of snap-fitting with the second mating structure and the female end is capable of snap-fitting with the first mating structure.

8. The electrode assembly of claim 5, wherein said first spine further comprises a stiffening material housed within said at least one first mating structure.

9. The electrode assembly of claim 2, wherein the first spine further comprises a stiffening material housed at least partially within said first end, and extending from the first end through at least a portion of said first spine.

10. The electrode assembly of claim 2, wherein the first spine further comprises at least one first mating structure, the second spine further comprises at least one second mating structure, and further comprising a mating element having a third mating structure and a fourth mating structure, wherein the third and fourth mating structures are each capable of mating with at least one of the first and second mating structures.

11. The electrode assembly of claim 2, wherein one or both of said first rail and said second rail are angled in a manner selected from the group consisting of toward the nearer of the first ends and the second ends of said first spine and said second spine, and away from the nearer of the first ends and the second ends of said first spine and said second spine.

12. The electrode assembly of claim 11, wherein the first rail and the second rail carry a mechanical load and the at least one electrode cross rail does not carry a mechanical load.

13. The electrode assembly of claim 2, wherein the thickness of the electrode assembly is substantially smaller than the width of the electrode assembly.

14. The electrode assembly of claim 2, wherein the at least one electrode has been attached to a body structure having a long axis and the at least one electrode, the first lead, and the second lead are structured to provide a controlled charge flow through the body structure in a direction selected from the group consisting of parallel to the long axis of the body structure and perpendicular to the long axis of the body structure.

15. An implantable medical system, comprising:
an implantable medical device comprising a controller to provide an electrical signal for performing neuromodulation; and
an electrode assembly comprising a first spine having a first end and a second end;
a second spine having a first end and a second end, wherein said first spine is generally opposite to said second spine, wherein the first spine and the second spine are joinable at the first end of said first spine and the first end of said second spine, and wherein said first spine and said second spine are formed of an electrically nonconductive material;
a first lead housed at least partially within said first spine, wherein said first lead extends from the first end of the first spine through at least a portion of the first spine;
a second lead housed at least partially within said second spine, wherein said second lead extends from the first end of the second spine through at least a portion of the second spine;
at least one electrode cross rail joining said first spine and said second spine, wherein said at least one electrode cross rail is formed of an electrically nonconductive material;
at least one electrode housed at least partially within the electrode cross rail and providing a route for electrical conduction between said first lead and the second lead;
a first rail joining said first spine and said second spine at a position closer to the first ends of the first and second spines relative to said at least one electrode cross rail, wherein said first rail is substantially formed of an electrically nonconductive material; and
a second rail joining said first spine and said second spine at a position closer to the second ends of said first and second spines relative to said at least one electrode cross rail, wherein said second rail is substantially formed of an electrically nonconductive material.

16. The implantable medical system of claim 15, wherein the neuromodulation is performed to treat a disorder selected from the group consisting of a mood disorder, an epilepsy disorder, an eating disorder, a hormonal disorder, a reproductive disorder, a metabolic disorder, a hearing disorder, a pain disorder, and a heart rhythm disorder.

17. An electrode assembly, comprising:
a first spine having at least one first mating structure,
a second spine having at least one second mating structure, wherein said first spine is generally opposite to said second spine, wherein said first mating structure is capable of mating with said second mating structure, and wherein said first spine and said second spine are formed substantially from an electrically nonconductive material capable of insulating a first body tissue from electrical current;

a first lead housed at least partially within said first spine, wherein said first lead extends from the first end of the first spine through at least a portion of the first spine;

a second lead housed at least partially within said second spine, wherein said second lead extends from the first end of the second spine through at least a portion of the second spine;

an electrode providing a route for electrical conduction between said first lead and the second lead, wherein the electrode is capable of providing electrical current to stimulate a second body tissue.

18. The electrode assembly of claim 17, wherein the second body tissue is a nerve.

19. The electrode assembly of claim 18, wherein the nerve is selected from the group consisting of the left vagus nerve and the right vagus nerve.

20. The electrode assembly of claim 17, wherein the first body tissue is body tissue surrounding a nerve.

* * * * *